United States Patent
Okabe

(10) Patent No.: US 10,424,181 B2
(45) Date of Patent: Sep. 24, 2019

(54) ELECTRONIC APPARATUS

(71) Applicant: KYOCERA CORPORATION, Kyoto (JP)

(72) Inventor: Ryosuke Okabe, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 153 days.

(21) Appl. No.: 15/552,792

(22) PCT Filed: Feb. 23, 2016

(86) PCT No.: PCT/JP2016/055129
§ 371 (c)(1),
(2) Date: Aug. 22, 2017

(87) PCT Pub. No.: WO2016/136687
PCT Pub. Date: Sep. 1, 2016

(65) Prior Publication Data
US 2019/0035247 A1 Jan. 31, 2019

(30) Foreign Application Priority Data
Feb. 23, 2015 (JP) .................... 2015-032562

(51) Int. Cl.
G08B 1/08 (2006.01)
G08B 21/04 (2006.01)
(Continued)

(52) U.S. Cl.
CPC ........ G08B 21/0453 (2013.01); A44C 5/0023 (2013.01); A61B 5/0002 (2013.01); A61B 5/7282 (2013.01); A61B 5/742 (2013.01); A61B 5/01 (2013.01); A61B 5/02416 (2013.01); A61B 5/02438 (2013.01); A61B 5/14542 (2013.01);
(Continued)

(58) Field of Classification Search
CPC . G08B 21/0453; A61B 5/0002; A61B 5/7282; A61B 5/742; A61B 2562/0257
See application file for complete search history.

(56) References Cited

U.S. PATENT DOCUMENTS 5,649,381 A * 7/1997 Studer .................. A44C 5/0015
368/281
6,177,873 B1 * 1/2001 Cragun .................... G01W 1/00
340/601

(Continued)

FOREIGN PATENT DOCUMENTS

JP 05-161610 A 6/1993
JP 2006-239084 A 9/2006
JP 2010-220948 A 10/2010

OTHER PUBLICATIONS

International Search Report/Written Opinion dated May 31, 2016, in corresponding International Application No. PCT/JP2016/055129 with Statement of Relevance of Non-English References.

Primary Examiner — Quang Pham
(74) Attorney, Agent, or Firm — Duane Morris LLP

(57) ABSTRACT

An electronic apparatus is worn on a body of a user. At least one processor determines whether biological information of the user contains an abnormality. An abnormality notification screen is displayed on a display when the at least one processor determines that the biological information contains the abnormality, the abnormality notification screen notifying an abnormality in the user.

10 Claims, 12 Drawing Sheets

(51) Int. Cl.
    *A61B 5/00*     (2006.01)
    *A44C 5/00*     (2006.01)
    *A61B 5/01*     (2006.01)
    *A61B 5/024*     (2006.01)
    *A61B 5/145*     (2006.01)

(52) U.S. Cl.
    CPC ....... *A61B 5/681* (2013.01); *A61B 2562/0257* (2013.01)

(56) References Cited

U.S. PATENT DOCUMENTS

| | | | | |
|---|---|---|---|---|
| 8,934,015 | B1* | 1/2015 | Chi | H04L 29/06476 348/158 |
| 9,069,333 | B1* | 6/2015 | Romans | G04G 13/02 |
| 9,715,363 | B2* | 7/2017 | Stewart, III | G06F 1/163 |
| 9,747,433 | B2* | 8/2017 | Patel | G06F 21/44 |
| 2006/0229520 | A1* | 10/2006 | Yamashita | A61B 5/0002 600/503 |
| 2006/0267760 | A1* | 11/2006 | Shecter | G08B 21/0216 340/539.15 |
| 2008/0001764 | A1* | 1/2008 | Douglas | G07C 9/00111 340/573.1 |
| 2008/0068932 | A1* | 3/2008 | Mosley | A61B 5/14532 368/281 |
| 2008/0266118 | A1* | 10/2008 | Pierson | A61B 5/0205 340/573.6 |
| 2009/0322513 | A1* | 12/2009 | Hwang | A61B 5/02055 340/539.12 |
| 2010/0190479 | A1* | 7/2010 | Scott | G06F 17/289 455/414.1 |
| 2011/0205851 | A1* | 8/2011 | Harris | G04G 9/0064 368/14 |
| 2012/0052802 | A1* | 3/2012 | Kasslin | H04W 48/12 455/41.2 |
| 2013/0109997 | A1* | 5/2013 | Linke | G06F 19/3418 600/549 |
| 2013/0122849 | A1* | 5/2013 | Doezema | A61B 5/002 455/404.1 |
| 2013/0135097 | A1* | 5/2013 | Doezema | G08B 21/0446 340/539.13 |
| 2013/0143519 | A1* | 6/2013 | Doezema | G08B 21/0446 455/404.2 |
| 2014/0218198 | A1* | 8/2014 | Muneshima | A61B 5/0205 340/573.1 |
| 2014/0225730 | A1* | 8/2014 | DePascale | G08B 21/0269 340/539.13 |
| 2014/0253322 | A1* | 9/2014 | Chapin | G08B 1/08 340/539.11 |
| 2014/0298859 | A1* | 10/2014 | Balboni | G01K 13/002 63/1.13 |
| 2014/0366123 | A1* | 12/2014 | DiBona | G06F 21/60 726/16 |
| 2015/0026647 | A1* | 1/2015 | Park | G06F 3/0488 715/863 |
| 2015/0035672 | A1* | 2/2015 | Housley | G08B 21/0275 340/539.13 |
| 2015/0039880 | A1* | 2/2015 | Aminzade | H04L 41/0816 713/100 |
| 2015/0046324 | A1* | 2/2015 | de la Cropte de Chanterac | G07F 7/0873 705/41 |
| 2015/0077245 | A1* | 3/2015 | Kaufman | G06F 19/3418 340/539.12 |
| 2015/0102208 | A1* | 4/2015 | Appelboom | G06F 19/3481 250/208.2 |
| 2015/0227245 | A1* | 8/2015 | Inagaki | G06F 3/0412 345/173 |
| 2015/0346024 | A1* | 12/2015 | Hingorani | G01J 1/4204 250/208.2 |
| 2015/0348495 | A1* | 12/2015 | Kim | G06F 3/0484 345/156 |
| 2016/0019817 | A1* | 1/2016 | Deokar | G08B 6/00 340/4.12 |
| 2016/0026211 | A1* | 1/2016 | Luna | G06F 3/0634 361/679.03 |
| 2016/0038055 | A1* | 2/2016 | Wheeler | A61B 5/0533 600/547 |
| 2016/0065655 | A1* | 3/2016 | Bentley | H04L 67/10 709/201 |
| 2016/0173359 | A1* | 6/2016 | Brenner | G06F 19/00 600/301 |
| 2016/0189517 | A1* | 6/2016 | Weast | G08B 21/02 340/573.1 |
| 2016/0255068 | A1* | 9/2016 | Pritchard | G06F 21/35 726/7 |
| 2017/0135449 | A1* | 5/2017 | Zhang | A44C 5/04 |

* cited by examiner

F I G. 1 5
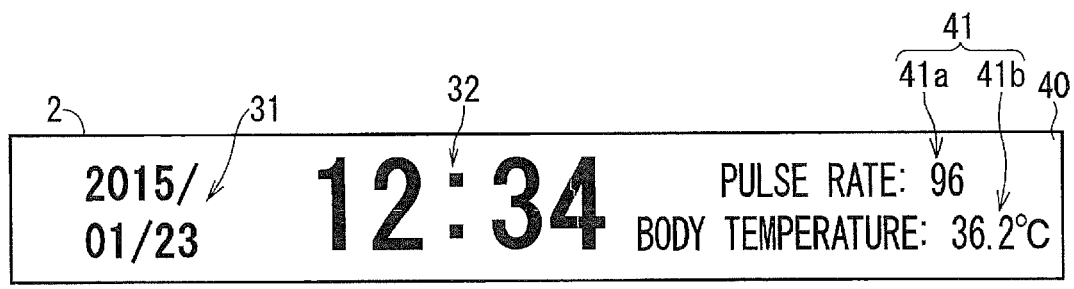

ELECTRONIC APPARATUS

TECHNICAL FIELD

The present invention relates to an electronic apparatus.

BACKGROUND ART

Techniques of obtaining biological information of a user have been conventionally disclosed.

SUMMARY

Problems to be Solved by the Invention

Upon occurrence of an abnormality in the user who uses an electronic apparatus, it will be convenient if the abnormality can be notified to the surrounding people using the electronic apparatus.

Means to Solve the Problems

An electronic apparatus is disclosed. According to one embodiment, an electronic apparatus includes: at least one processor configured to determine whether biological information of a user contains an abnormality; and a display. An abnormality notification screen is displayed on the display when the at least one processor determines that the biological information contains the abnormality, the abnormality notification screen notifying an abnormality in the user.

Effects of the Invention

The abnormality in the user can be notified to the surrounding people.

BRIEF DESCRIPTION OF DRAWINGS

FIG. 15 schematically illustrates an example normal screen.

DESCRIPTION OF EMBODIMENTS

[Appearance of Electronic Apparatus]

Figure 1:
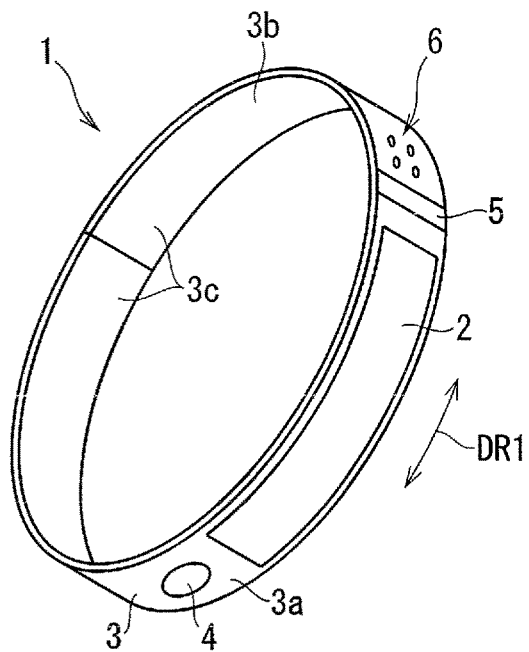
FIG. 1 illustrates a perspective view schematically showing an example appearance of an electronic apparatus.
Figure 2:
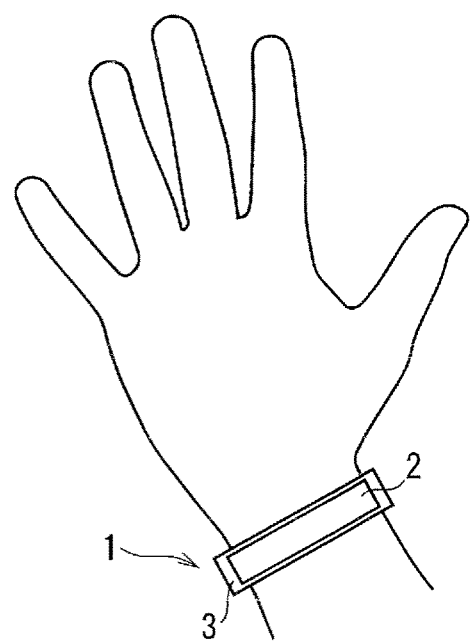
FIG. 2 illustrates a state in which the electronic apparatus is worn.
Figure 3:
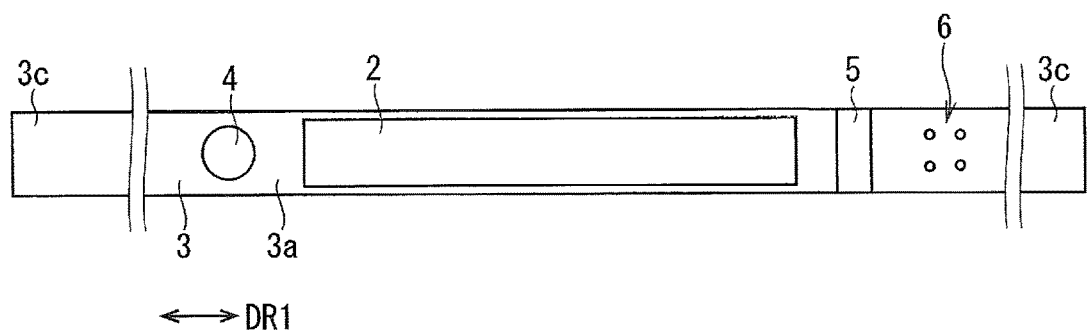
FIG. 3 illustrates an anterior view schematically showing an example appearance of the electronic apparatus.
Figure 4:
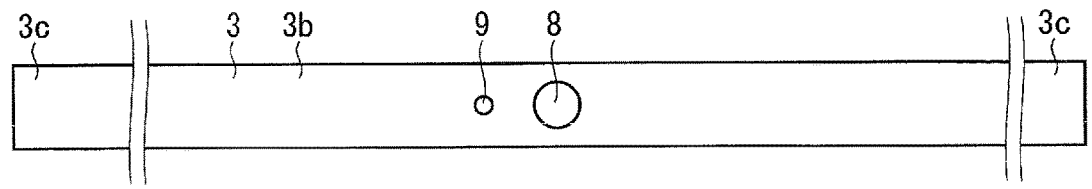
FIG. 4 illustrates a rear view schematically showing an example appearance of the electronic apparatus.

FIG. 1 illustrates a perspective view schematically showing an example appearance of an electronic apparatus 1. FIG. 2 illustrates a state in which the electronic apparatus 1 is worn by the user. FIGS. 3 and 4 illustrate an anterior view and a rear view, respectively, which schematically show example appearances of the electronic apparatus 1 when the electronic apparatus 1 is not worn.

The electronic apparatus 1 is worn by the user who uses the electronic apparatus 1. As illustrated in FIG. 1, the electronic apparatus 1 includes a case 3. The case 3 is a portion of an exterior of the electronic apparatus 1. The case 3 is made of a flexible material, for example, a rubber or a resin. The electronic apparatus 1 can be bent toward a rear surface 3b side of the case 3 along a longitudinal direction DR1 of the electronic apparatus 1. The electronic apparatus 1 becomes ring-shaped by connecting both end portions 3c of the case 3 in the longitudinal direction DR1 to each other. As illustrated in FIG. 2, the electronic apparatus 1 becomes ring-shaped, and is worn on, for example, the wrist of the user. As illustrated in FIGS. 3 and 4, the electronic apparatus 1 is slender plate-shaped and approximately rectangular in a plan view when it is not worn by the user. The case 3 is also called a band part or a belt part.

In the electronic apparatus 1, the both end portions 3c of the case 3 are connected to each other, for example, via respective magnets (not illustrated) provided in the both end portions 3c. Accordingly, the electronic apparatus 1 becomes ring-shaped, and is worn by the user.

The method for connecting the both end portions 3c of the case 3 is not limited to such. The both end portions 3c of the case 3 may be connected to each other, for example, similarly as a strap for a watch. Specifically, a through hole may be provided on one of the end portions 3c of the case 3, and a buckle for fastening the through hole may be provided on the other end portion 3c of the case 3.

Furthermore, although the electronic apparatus 1 is worn on the wrist of the user in the exemplification of FIG. 2, it may be worn on another part of the user. The electronic apparatus 1 may be worn on, for example, the arm or the leg of the user. Furthermore, the electronic apparatus 1 may be, for example, necklace-shaped and worn on the neck of the user. Since the electronic apparatus 1 obtains biological information of the user as described below, it is worn on a part of the user that is appropriate for obtaining the biological information.

Using a flexible material such as a rubber or a resin as a material for the case 3 can relatively easily fit the case 3, for example, around the wrist of the user. Accordingly, the biological information of the user is easily obtained. The material for the case 3 is not limited to the flexible material such as a rubber or a resin but may be a material, for example, a relatively hard resin such as acryl, a metal, or ceramic as long as the biological information of the user can be obtained. If these relatively hard materials are used, the electronic apparatus 1 may have a shape of a bangle as jewelry, or a shape of an open chain belt used in a watch.

As illustrated in FIGS. 1 and 3, a display 2, an operation button 4, a light emitting unit 5, and a sound output unit 6 are provided on a front surface 3a of the case 3. Furthermore, as illustrated in FIG. 4, a biological information obtaining unit 8, and a proximity sensor 9 are provided on a rear surface 3b of the case 3.

The display 2 is provided at the center part of the front surface 3a of the case 3. The display 2 is, for example, an electronic paper. The light emitting unit 5 includes, for example, a light emitting diode, and can output light to the outside of the electronic apparatus 1. The sound output unit 6 includes a speaker, and speaker holes through which the sound output by the speaker is taken out of the electronic apparatus 1. The speaker holes are provided on the front surface 3a of the case 3. The operation button 4 is an operation part to be operated by the user. The operation button 4 is pressed by the user. The operation button 4, the display 2, the light emitting unit 5, and the sound output unit 6 are aligned along the longitudinal direction DR1 from the left on the front surface 3a of the case 3. The order of the positions of these constituent elements along the longitudinal direction DR1 is not limited to such.

The biological information obtaining unit 8 is provided at the center part of the rear surface 3b of the case 3. The biological information obtaining unit 8 can obtain biological information of the user. The biological information obtaining unit 8 can obtain, for example, a pulse rate of the user. The proximity sensor 9 is aligned side by side with the biological information obtaining unit 8 along the longitudinal direction DR1. The proximity sensor 9 can detect the proximity of an object. The positions of the proximity sensor 9 and the biological information obtaining unit 8 are not limited to these but may be aligned, for example, in a vertical direction relative to the longitudinal direction DR1.

[Electrical Configuration of Electronic Apparatus]

Figure 5:
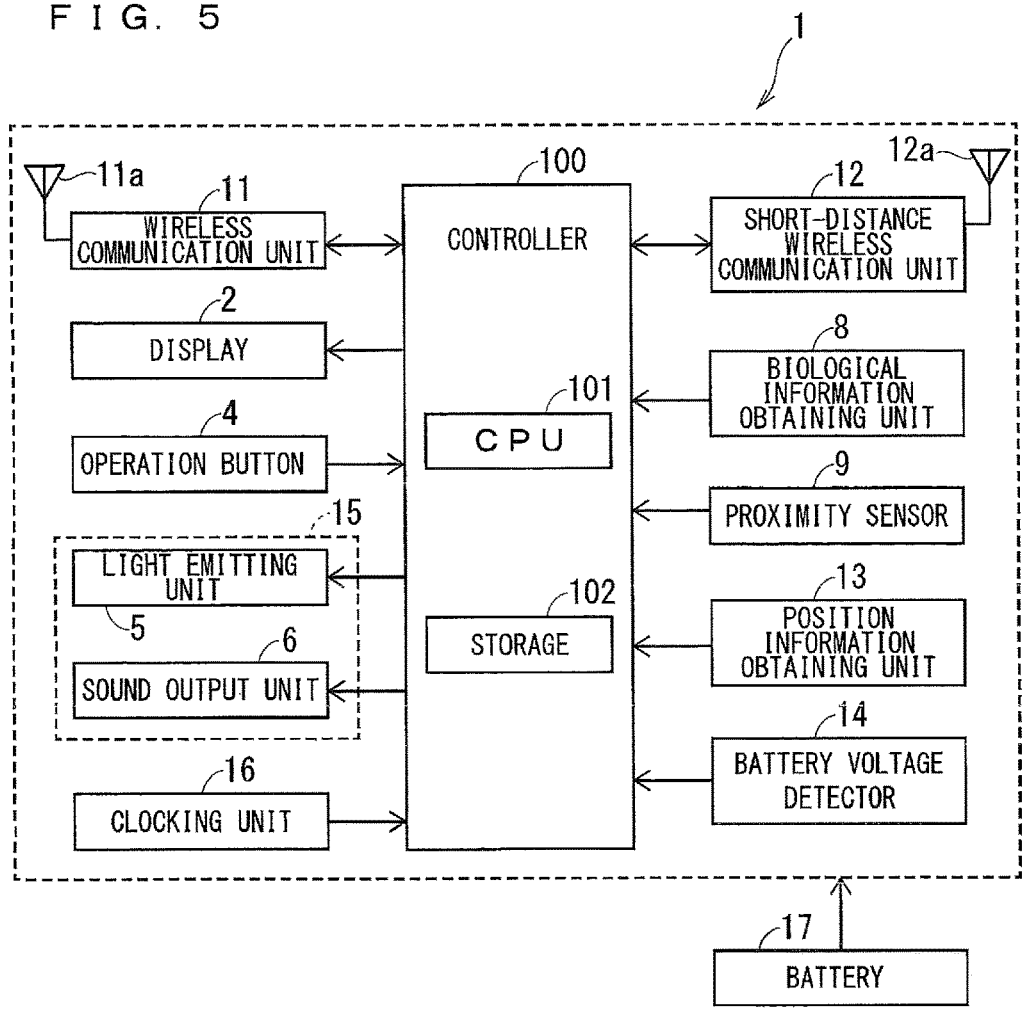
FIG. 5 illustrates an example electrical configuration of the electronic apparatus.

FIG. 5 illustrates a block diagram showing an example electrical configuration of the electronic apparatus 1. The electronic apparatus 1 includes various constituent elements other than the display 2, the operation button 4, the light emitting unit 5, the sound output unit 6, the biological information obtaining unit 8, and the proximity sensor 9. Specifically, the electronic apparatus 1 includes a controller 100, a wireless communication unit 11, a short-distance wireless communication unit 12, a position information obtaining unit 13, a battery voltage detector 14, and a clocking unit 16 as illustrated in FIG. 5. Furthermore, the electronic apparatus 1 is connected to a battery 17 to supply power to the electronic apparatus 1. The case 3 accommodates these constituent elements including the battery 17.

The controller 100 is a kind of a computer, and includes, for example, a central processing unit (CPU) 101 and a storage 102. The controller 100 can manage the overall operations of the electronic apparatus 1 by controlling the other constituent elements of the electronic apparatus 1. In other words, the controller 100 is a control circuit.

The storage 102 includes a non-transitory recording medium that can be read by the CPU 101, such as a read only memory (ROM) and a random access memory (RAM). The storage 102 stores, for example, a main program that is a control program and a plurality of application programs for controlling the electronic apparatus 1, specifically, respective constituent elements included in the electronic apparatus 1 such as the wireless communication unit 11 and the display 2. Various functions of the controller 100 can be implemented by causing the CPU 101 to execute the various programs in the storage 102. In other words, the storage 102 is a storage circuit.

The storage 102 may include a non-transitory computer-readable recording medium other than the ROM and the RAM. The storage 102 may include, for example, a compact hard disk drive and a solid-state drive (SSD). Furthermore, a part or the whole of the functions of the controller 100 may be implemented by hardware that does not require software for implementing the functions of the hardware.

The wireless communication unit 11 is a communication circuit including an antenna 11a. The wireless communication unit 11 can perform wireless communication using the antenna 11a in conformity with a wireless communication standard such as wideband code division multiple access (W-CDMA) or Long Term Evolution (LTE). The wireless communication unit 11 can perform an amplification process and down-conversion on a signal received by the antenna 11a and then output the signal to the controller 100. The controller 100 can perform, for example, a demodulation process on the received signal to be input, and acquire information included in the received signal. Furthermore, the wireless communication unit 11 can perform up-conversion and the amplification process on a transmission signal generated by the controller 100, and then wirelessly transmit the transmission signal after the processes from the antenna 11a.

The short-distance wireless communication unit 12 is a communication circuit including an antenna 12a. The short-distance wireless communication unit 12 can perform wireless communication using the antenna 12a. The short-distance wireless communication unit 12 has a narrower communication area than that of the wireless communication unit 11. The short-distance wireless communication unit 12 can perform communication in conformity with, for example, Bluetooth (trademark).

The display 2 can display various information such as characters, symbols, figures, or images under the control of the controller 100. Information displayed on the display 2 can be visually recognized by the user.

Upon being pressed by the user, the operation button 4 can output an operation signal to the controller 100. Upon receipt of the operation signal, the controller 100 can perform a predetermined process. This predetermined process will be described later.

The controller 100 controls the light emitting unit 5 and the sound output unit 6. According to the present disclosure, the light emitting unit 5 and the sound output unit 6 form an output unit 15 capable of outputting light and sound outside of the electronic apparatus 1.

The biological information obtaining unit 8 includes, for example, a pulse wave sensor. The biological information obtaining unit 8 can measure a pulse rate of the user based on the pulse wave sensed by the pulse wave sensor. The biological information obtaining unit 8 can output the measured pulse rate of the user to the controller 100. The pulse wave sensor includes, for example, a light source and a light receiving element. In the pulse wave sensor, the light source emits light to the skin of the user, and the light receiving element receives the reflected light. Since the reflected light varies according to change in the bloodstream, the biological information obtaining unit 8 can obtain a pulse rate based on variation in the reflected light. The biological information is, for example, information that varies according to a health condition of the user. The biological information obtained by the biological information obtaining unit 8 is not limited to a pulse rate. The biological information obtaining unit 8 may obtain, for example, a body temperature, a blood pressure, or a blood oxygen level. Furthermore, the biological information obtaining unit 8 may obtain plural kinds of biological information.

The position information obtaining unit 13 can obtain the current position of the electronic apparatus 1. The position information obtaining unit 13 is, for example, a device using global positioning system (GPS), and is also called a GPS receiver. The position information obtaining unit 13 is a circuit capable of receiving a GPS signal from a GPS satellite and obtaining position information indicating the current position of the electronic apparatus 1, based on the GPS signal. The position information includes, for example, latitude information and longitude information.

The proximity sensor 9 is, for example, an infrared type proximity sensor. The proximity sensor 9 can output a detection signal to the controller 100 when an object comes in proximity to the proximity sensor 9 within a predetermined distance from the proximity sensor 9. The controller 100 can detect the object being in proximity to the electronic apparatus 1, based on the detection signal from the proximity sensor 9. As described above, since the proximity sensor 9 is provided on the rear surface 3b of the case 3, the electronic apparatus 1 can detect the body of the user being in proximity to the electronic apparatus 1 through the proximity sensor 9.

The battery 17 can output the power for the electronic apparatus 1. The power output from the battery 17 is supplied to the respective electronic components, for example, the controller 100 and the wireless communication unit 11 that are included in the electronic apparatus 1. The battery 17 is, for example, a lithium ion secondary battery. The battery 17 is charged in a non-contact manner through, for example, electromagnetic induction.

The battery voltage detector 14 is a circuit capable of detecting an output voltage of the battery 17 (may be hereinafter referred to as "battery voltage") and notifying the controller 100 of the output voltage. The controller 100 can compare the battery voltage detected by the battery voltage detector 14 with a threshold, and perform a process according to a result of the comparison, which will be described later.

The clocking unit 16 is a circuit capable of clocking the current date as well as the current time. The clocking unit 16 includes a real time clock (RTC). The clocking unit 16 can output, to the controller 100, time information indicating the clocked time and date information indicating the clocked date.

Figure 6:
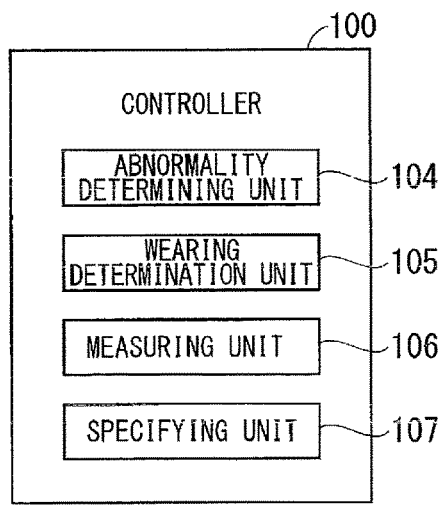
FIG. 6 illustrates example functional blocks formed in a controller.

FIG. 6 illustrates a block diagram showing example functional blocks formed in the controller 100. The controller 100 includes, as the functional blocks, an abnormality determining unit 104, a wearing determination unit 105, a measuring unit 106, and a specifying unit 107. Each of the abnormality determining unit 104, the wearing determination unit 105, the measuring unit 106, and the specifying unit 107 may be implemented by a hardware circuit that does not require software for implementing the functions of the hardware circuit.

The abnormality determining unit 104 can determine whether the biological information of the user that is obtained by the biological information obtaining unit 8 contains an abnormality. The abnormality determining unit 104 receives a pulse rate of the user. When, for example, the pulse rate of the user becomes zero, the abnormality determining unit 104 determines that the biological information of the user contains an abnormality.

The wearing determination unit 105 can determine whether the electronic apparatus 1 is worn by the user. When the proximity sensor 9 detects the proximity of an object, the wearing determination unit 105 determines that the electronic apparatus 1 is worn on the wrist of the user.

The specifying unit 107 can specify a time at which an abnormality has occurred in the user (may be hereinafter referred to as "abnormality occurrence time"). Specifically, the specifying unit 107 specifies a time at which the abnormality determining unit 104 determines that the biological information of the user contains the abnormality, based on the time information output by the clocking unit 16, and determines the specified time as an abnormality occurrence time. The measuring unit 106 can measure an elapsed time since occurrence of the abnormality in the user. Specifically, the measuring unit 106 measures an elapsed time since the abnormality occurrence time specified by the specifying unit 107, based on the time information output by the clocking unit 16.

[Operations of Electronic Apparatus]

The electronic apparatus 1 is worn on the body of the user, and obtains biological information of the user. When the abnormality determining unit 104 determines that the biological information of the user contains an abnormality, the electronic apparatus 1 notifies the abnormality in the user to the surroundings. The operations of the electronic apparatus 1 will be hereinafter described in detail.

Figure 7:
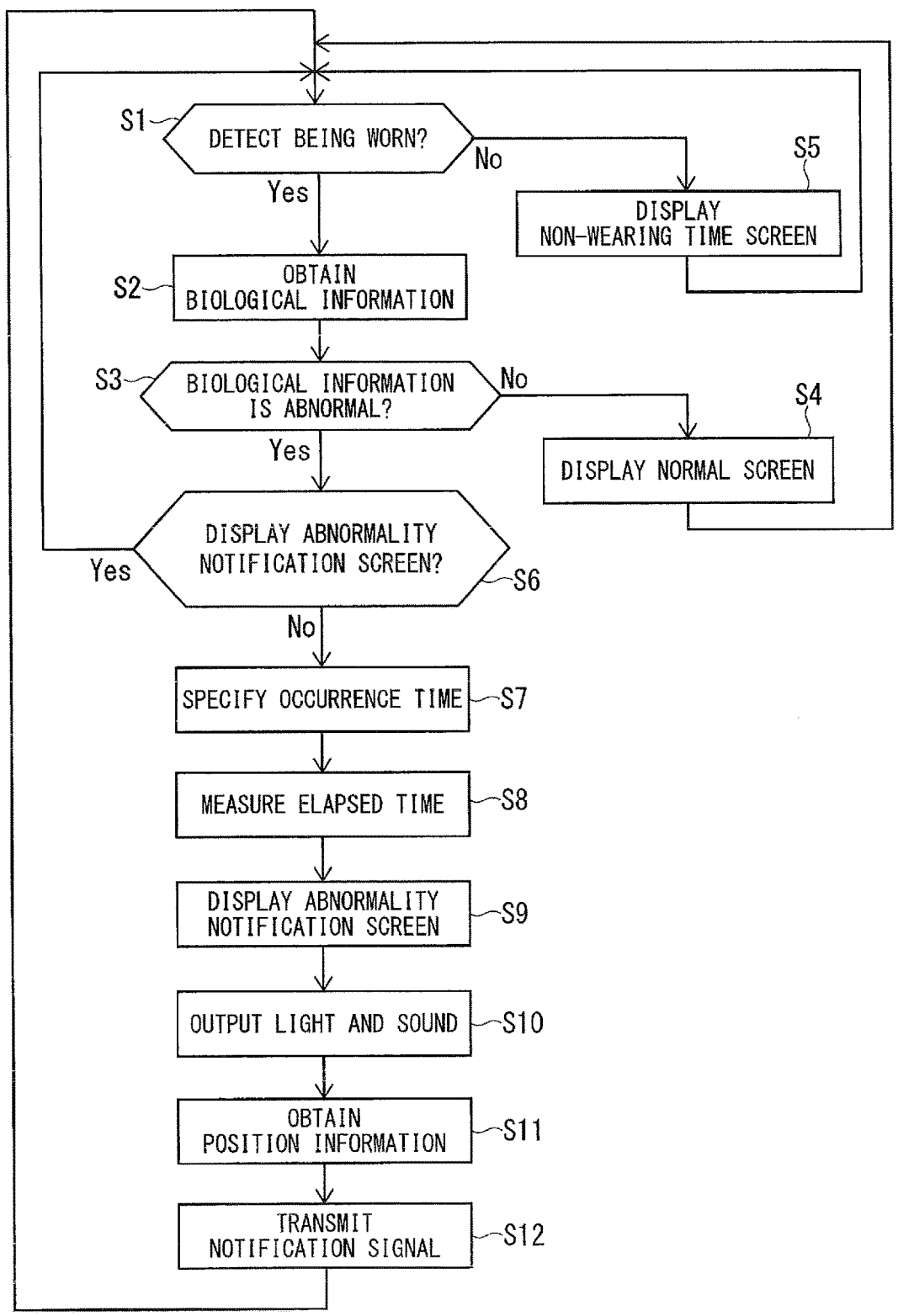
FIG. 7 illustrates a flowchart showing example operations of the electronic apparatus.

FIG. 7 illustrates a flowchart showing example operations of the electronic apparatus 1. At Step S1, first, the wearing determination unit 105 determines whether the electronic apparatus 1 is worn by the user, based on a detection signal from the proximity sensor 9. Step S1 is performed at predetermined time intervals.

Figure 8:
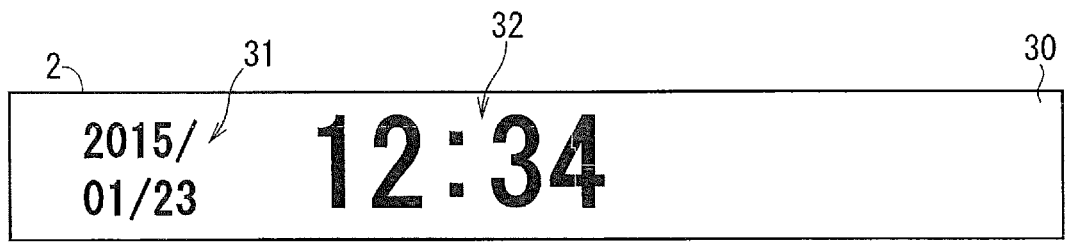
FIG. 8 schematically illustrates an example non-wearing time screen.

If Step S1 yields a negative determination, Step S5 is performed. At Step S5, the controller 100 causes the display 2 to display a non-wearing time screen 30. The non-wearing time screen 30 is a screen displayed on the display 2 in a state where the electronic apparatus 1 is not worn by the user. FIG. 8 schematically illustrates an example of the non-wearing time screen 30. As illustrated in FIG. 8, the non-wearing time screen 30 includes date information 31 indicating the current date and time information 32 indicating the current time. The clocking unit 16 obtains such information.

After Step S5, Step S1 is performed again. Until it is determined at Step S1 that the electronic apparatus 1 is worn by the user, Steps S1 and S5 are repeatedly performed. In other words, the non-wearing time screen 30 is displayed on the display 2 until it is determined at Step S1 that the electronic apparatus 1 is worn by the user.

If Step S1 yields a positive determination, Step S2 is performed. At Step S2, the controller 100 causes the biological information obtaining unit 8 to start obtaining biological information. The biological information obtaining unit 8 obtains the biological information of the user, and outputs the biological information to the controller 100. In this embodiment, the biological information obtaining unit 8 obtains a pulse rate of the user, and outputs it to the abnormality determining unit 104.

Next at Step S3, the abnormality determining unit 104 determines whether the biological information of the user contains an abnormality. When, for example, the pulse rate of the user is zero, the abnormality determining unit 104 determines that the biological information of the user contains an abnormality.

Figure 9:
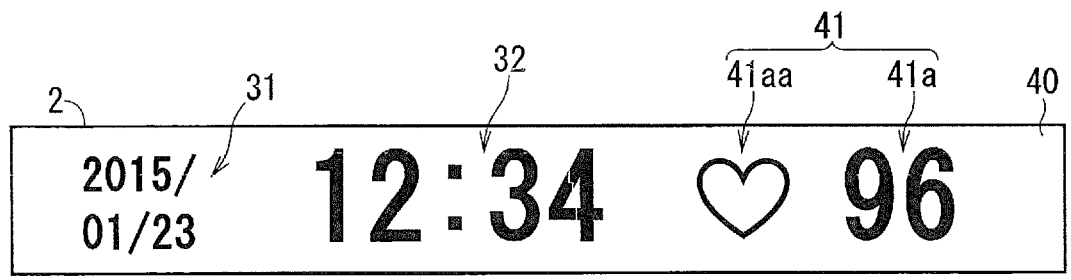
FIG. 9 schematically illustrates an example normal screen.

If Step S3 yields a negative determination, Step S4 is performed. At Step S4, the controller 100 causes the display 2 to display a normal screen 40. The normal screen 40 is a screen displayed when the abnormality determining unit 104 determines that the biological information of the user does not contain an abnormality, in a state where the electronic apparatus 1 is worn by the user. FIG. 9 schematically illustrates an example of the normal screen 40. As illustrated in FIG. 9, the normal screen 40 further includes information 41 including biological information of the user, in comparison with the non-wearing time screen 30.

The information 41 includes a number 41a indicating a pulse rate (biological information) obtained by the biological information obtaining unit 8, and a graphic symbol 41aa representing that the number 41a is a pulse rate. The graphic symbol 41aa is, for example, heart-shaped. The user can check the own biological information by viewing the information 41.

After Step S4, Step S1 is performed again. In other words, the normal screen 40 is displayed on the display 2 during no occurrence of abnormality in the user, in a state where the electronic apparatus 1 is worn by the user.

If Step S3 yields a positive determination, a series of processes from Step S6 to Step S12 to be described later are performed. This series of processes are processes for notifying that the user has abnormality.

At Step S6, first, the controller 100 determines whether an abnormality notification screen to be described later is displayed on the display 2. If Step S6 yields a positive determination, Step S1 is performed. If Step S6 yields a negative determination, at Step S7, the specifying unit 107 specifies a time at which the abnormality has occurred in the user. Next at Step S8, the measuring unit 106 measures an elapsed time since the occurrence of the abnormality in the user.

Figure 10:
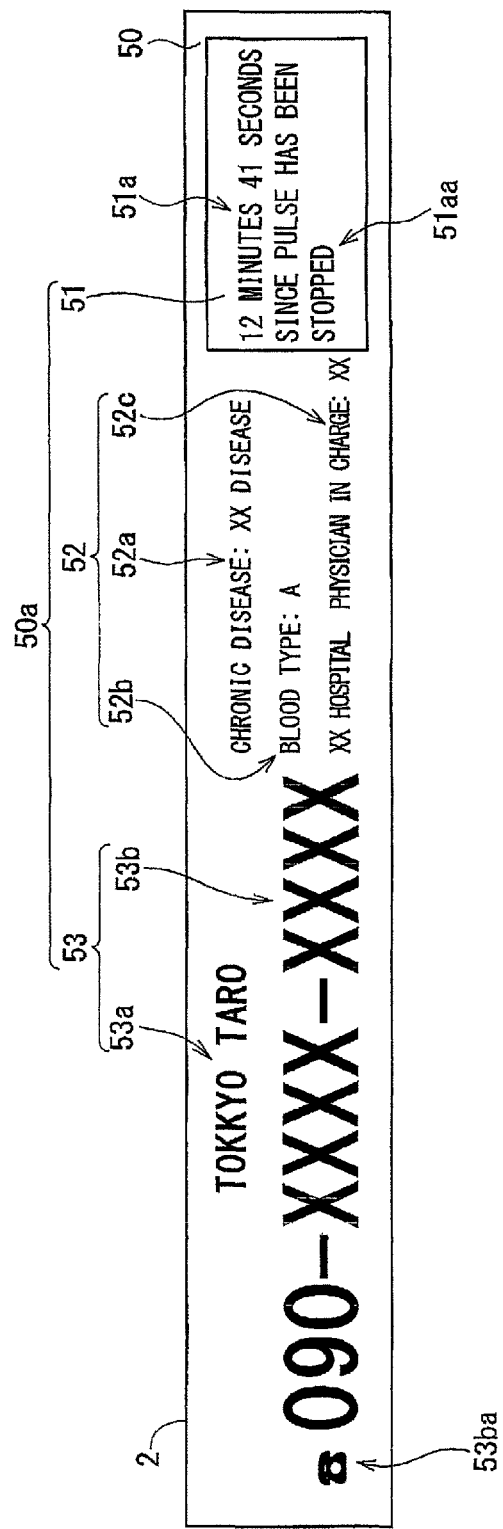
FIG. 10 schematically illustrates an example abnormality notification screen.

At Step S9, the controller 100 causes the display 2 to display an abnormality notification screen 50 for notifying an abnormality in the user. FIG. 10 schematically illustrates an example of the abnormality notification screen 50. As illustrated in FIG. 10, the abnormality notification screen 50 includes useful information 50a that is useful in taking an action for the user with the abnormality. Accordingly, a person who views the abnormality notification screen 50 can take an appropriate action for the user with the abnormality, based on the useful information 50a.

In the exemplification of FIG. 10, the useful information 50a includes first information 51, second information 52, and third information 53. The first information 51 is abnormality notification information for notifying the abnormality in the user. Furthermore, the first information 51 is also useful information for a person who takes an action for the user to understand an abnormal condition of the user. In the exemplification of FIG. 10, the first information 51 includes a character string 51aa including an elapsed time 51a since occurrence of the abnormality in the user. The character string 51aa indicates what kind of elapsed time the elapsed time 51a included therein is. Accordingly, the person who takes an action for the user can take an appropriate action according to the elapsed time 51a. Examples of such an action include treating the user according to the elapsed time 51a and calling an ambulance.

The second information 52 is useful information for a person, for example, an ambulance crew, to treat the user. In the exemplification of FIG. 10, the second information 52 includes a chronic disease name 52a and a blood type 52b of the user, and attending physician information 52c relevant to an attending physician of the user. The attending physician information 52c includes the name of the attending physician and the name of a hospital where the attending physician works. Displaying the second information 52 on the display 2 allows, for example, an ambulance crew or a doctor at an ambulance destination to take a more appropriate action for the user, for example, treat the user according to the second information.

The third information 53 is useful information when the person who takes an action for the user informs the abnormality in the user. In the exemplification of FIG. 10, the third information 53 includes a user name 53a, an emergency contact 53b, and a graphic symbol 53ba representing that the emergency contact 53b is a telephone number. Accordingly, the person who takes an action for the user can take a more appropriate action for the user, for example, by informing the abnormality in the user to the emergency contact 53b of the user.

In other words, each of the first information 51, the second information 52, and the third information 53 is user information on the user. Thus, the abnormality notification screen 50 includes user information. On the other hand, neither the non-wearing time screen 30 nor the normal screen 40 includes user information except for the biological information of the user. Accordingly, it is possible to prevent the user information excluding the biological information from leaking to the surroundings, when the electronic apparatus 1 is not worn by the user and the user does not have any abnormality.

At Step S10, the controller 100 causes the output unit 15 to output light and sound. Specifically, the light emitting unit 5 and the sound output unit 6 included in the output unit 15 output the light and the sound, respectively. The light emitting unit 5 notifies the surroundings of the abnormality in the user by emitting light, for example, in a predetermined light emitting pattern that is pre-registered. The sound output unit 6 notifies the surroundings of the abnormality in the user by outputting predetermined sound. The predetermined sound may be voice or sound other than the voice. At Step S10, the output unit 15 may output any one of the light and the sound.

At Step S11, the controller 100 causes the position information obtaining unit 13 to obtain position information of the electronic apparatus 1. Next at Step S12, the controller 100 causes the wireless communication unit 11 to transmit a notification signal for notifying the abnormality in the user. The notification signal is transmitted via, for example, an electronic mail. A mail address of a destination to which the notification signal is transmitted is pre-registered in the storage 102 together with, for example, the useful information 50a as an emergency notification destination to be notified when the user has any abnormality. The notification signal includes, for example, the position information obtained at Step S11. Accordingly, the electronic apparatus that has received the notification signal displays the position information included in the notification signal, so that a person who uses the electronic apparatus (for example, a family member of the user) at the emergency notification destination can know the abnormality in the user of the electronic apparatus 1 and locate the position of the user. The notification signal may include the biological information of the user.

After Step S12, Step S1 is performed again. The abnormality notification screen 50 is displayed on the display 2 during the occurrence of abnormality in the user, in a state where the electronic apparatus 1 is worn by the user. While the abnormality notification screen 50 is displayed, the elapsed time 51a in the abnormality notification screen 50 is updated whenever necessary.

When the biological information of the user no longer contains an abnormality after the abnormality determining unit 104 determines that the biological information of the user contains an abnormality, that is, if Step S3 yields a negative determination, the normal screen 40 is displayed on the display 2 at Step S4, instead of the abnormality notification screen 50. Here, the wireless communication unit 11 may transmit a signal for notifying that the user is no longer abnormal to the emergency notification destination via, for example, an electronic mail.

An order for performing Step S9, Step S10, and Steps consisting of Steps S11 and S12 may be shuffled. Furthermore, at least one of Steps S10, Step S11, and S12 may be eliminated.

The second information 52 and the third information 53 included in the abnormality notification screen 50 are, for example, input to the electronic apparatus 1 using the short-distance wireless communication unit 12, and stored in the storage 102. Specifically, the second information 52 and the third information 53 are input to an electronic apparatus, such as a personal computer, which can communicate with the short-distance wireless communication unit 12. The electronic apparatus transmits the input second information 52 and third information 53 to the short-distance wireless communication unit 12. In the electronic apparatus 1, the second information 52 and the third information 53 received by the short-distance wireless communication unit 12 are stored in storage 102.

The method of inputting the second information 52 and the third information 53 to the electronic apparatus 1 may be other methods. If, for example, the electronic apparatus 1 can communicate with an external apparatus in conformity with Universal Serial Bus (USB), the second information 52 and the third information 53 may be input to the electronic apparatus 1 using the USB.

Furthermore, the electronic apparatus 1 is sold in, for example, a hospital. Here, for example, a doctor at the hospital in which the electronic apparatus 1 is sold inputs, to the electronic apparatus 1, the second information 52 and the third information 53 on the user of the electronic apparatus 1 using, for example, a personal computer. The user of the electronic apparatus 1 may input the second information 52 and the third information 53 to the electronic apparatus 1.

Furthermore, since a battery voltage is used as a power voltage for the electronic apparatus 1, the electronic apparatus 1 cannot perform most of the functions with significant decrease in the battery voltage. When, for example, the battery voltage is lower than a predetermined value, the electronic apparatus 1 cannot drive the display 2, wirelessly communicate with another device using the wireless communication unit 11, or obtain position information using the position information obtaining unit 13.

On the other hand, the display 2 is an electronic paper. The electronic paper does not require power for maintaining the display. Thus, even when the battery voltage is lower than a predetermined value and the display 2 is not driven by the controller 100, in other words, even when the display 2 is not supplied with sufficient power, the electronic paper can maintain the display. Thus, in the case where a screen such as the abnormality notification screen 50 is displayed on the display 2, even when the battery voltage is lower than the predetermined value and the display 2 is not driven by the controller 100, the screen such as the abnormality notification screen 50 can be continuously displayed on the display 2. The display 2 may be a display other than the electronic paper, for example, a liquid crystal display or an organic EL display.

Furthermore, when the electronic apparatus 1 includes a vibrator that vibrates the case 3, the electronic apparatus 1 may notify the abnormality in the user to the user himself or herself using the vibrator. For example, the controller 100 may cause the vibrator to vibrate in a vibration pattern registered as a pattern for notification vibration to vibrate the whole case 3, so that the user may be notified of the abnormality in the biological information. A conceivable vibrator is, for example, a compact motor or a piezoelectric element.

[Operations of Battery Voltage Detector]

The controller 100 determines whether the battery voltage detected by the battery voltage detector 14 is smaller than a threshold when the abnormality notification screen 50 is displayed on the display 2. Then, the controller 100 causes the display 2 to display the abnormality notification screen 50 including an occurrence time 51$b$ instead of the elapsed time 51$a$ when determining that the battery voltage is smaller than the threshold.

Figure 11:
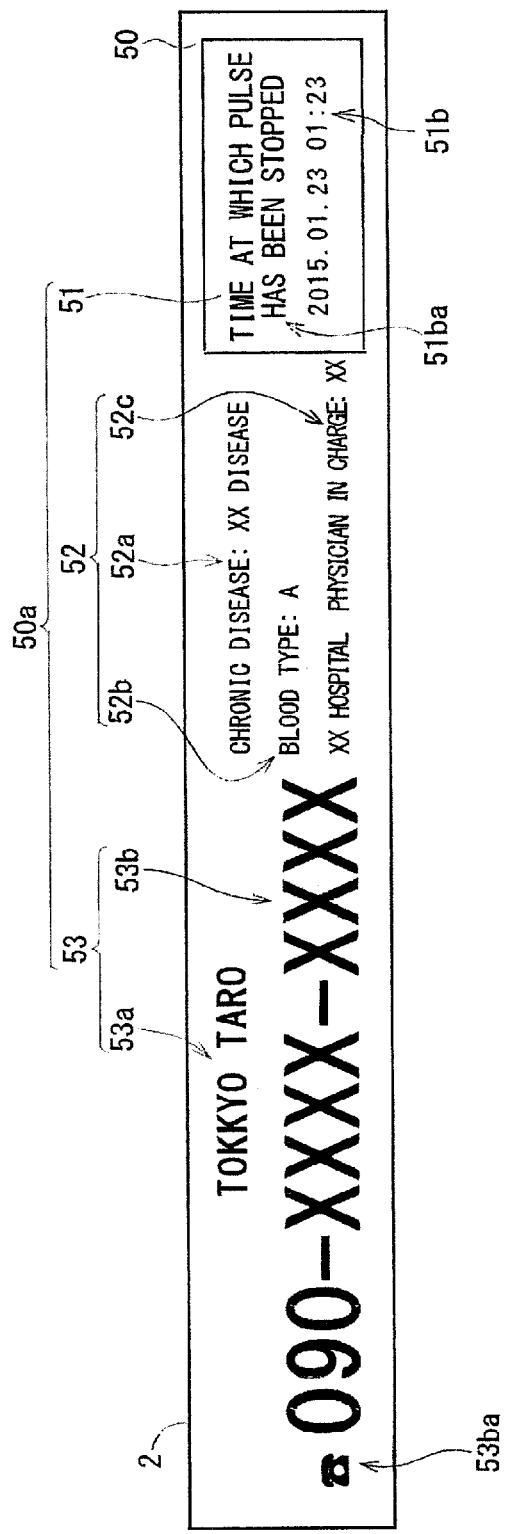
FIG. 11 schematically illustrates an example abnormality notification screen.

FIG. 11 schematically illustrates an example of the abnormality notification screen 50 including the occurrence time 51$b$. As illustrated in FIG. 11, the first information 51 includes the occurrence time 51$b$ and a character string 51$ba$ indicating what kind of time the occurrence time 51$b$ is, instead of the character string 51$aa$ including the elapsed time 51$a$.

Here, when the battery voltage becomes smaller, the controller 100 cannot update the elapsed time 51$a$. When the abnormality notification screen 50 including the elapsed time 51$a$ that is not updated is displayed, the elapsed time 51$a$ that is incorrect is notified to the surroundings. According to this embodiment, since the abnormality notification screen 50 including the occurrence time 51$b$ instead of the elapsed time 51$a$ is displayed when the battery voltage is smaller than the threshold, it is possible to suppress notification of the elapsed time 51$a$ that is incorrect and notify information useful in understanding an abnormal condition of the user. The abnormality notification screen 50 including the occurrence time 51$b$ as illustrated in FIG. 11 may be displayed on the display 2, irrespective of a value of the battery voltage.

[Notification of Abnormality Using Operation Button]

As described above, when the abnormality determining unit 104 determines that the biological information of the user contains an abnormality, the electronic apparatus 1 notifies the abnormality in the user. In addition to this, the electronic apparatus 1 notifies the abnormality in the user when the operation button 4 is operated in this embodiment. The operation on the operation button 4 for notifying the abnormality in the user may be referred to as an abnormality notification operation.

Figure 12:
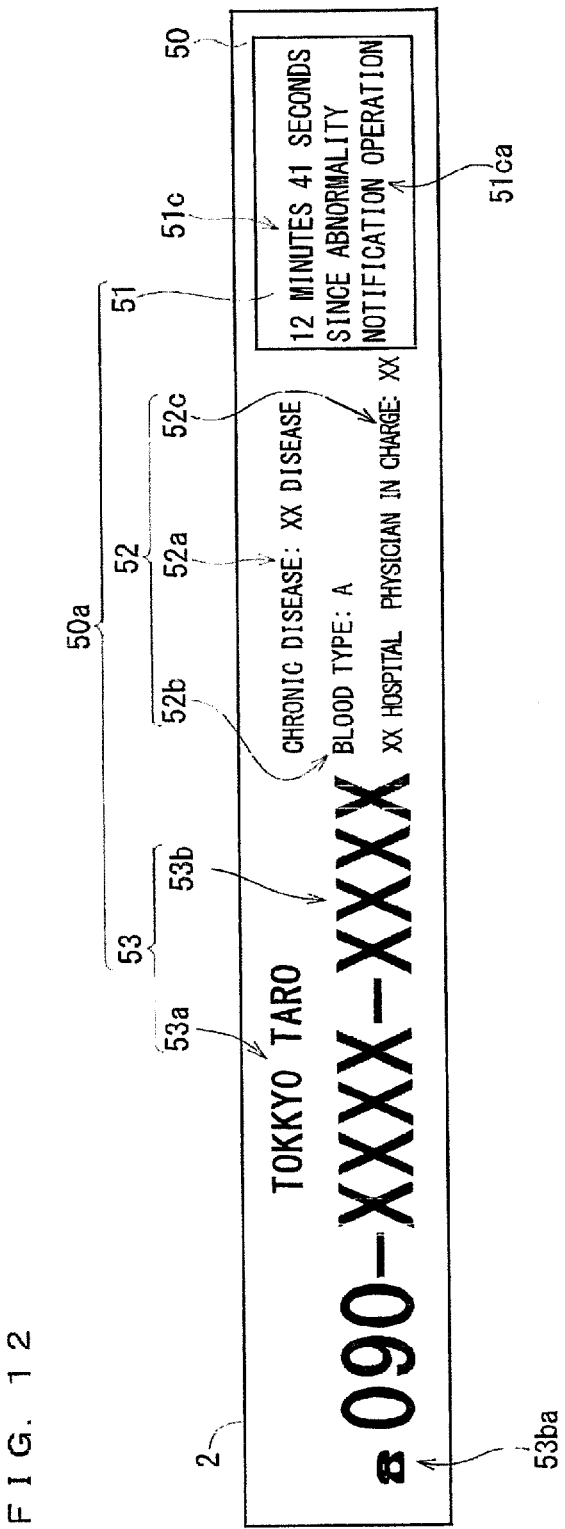
FIG. 12 schematically illustrates an example abnormality notification screen.

Upon the operation button 4 being pressed, the controller 100 causes the display 2 to display the abnormality notification screen 50 illustrated in FIG. 12. In the abnormality notification screen 50 illustrated in FIG. 12, the first information 51 includes a character string 51$ca$ including an elapsed time 51$c$ since an abnormality notification operation. The character string 51$ca$ indicates what kind of elapsed time the elapsed time 51$c$ included therein is. Furthermore, the controller 100 causes the output unit 15 to output light and sound similarly as Step S10 as well as displays the abnormality notification screen 50.

As such, upon operation on the operation button 4, the electronic apparatus 1 notifies the abnormality in the user using the display 2 and the output unit 15. Accordingly, the user can voluntarily make the electronic apparatus 1 notify the abnormality when the abnormality occurs in himself or herself.

Upon the operation button 4 being pressed in a state where the abnormality notification screen 50 illustrated in FIG. 12 is displayed, the electronic apparatus 1 may stop notifying the abnormality in the user. Here, the normal screen 40 may be displayed on the display 2 instead of the abnormality notification screen 50.

[Variation]

Figure 13:
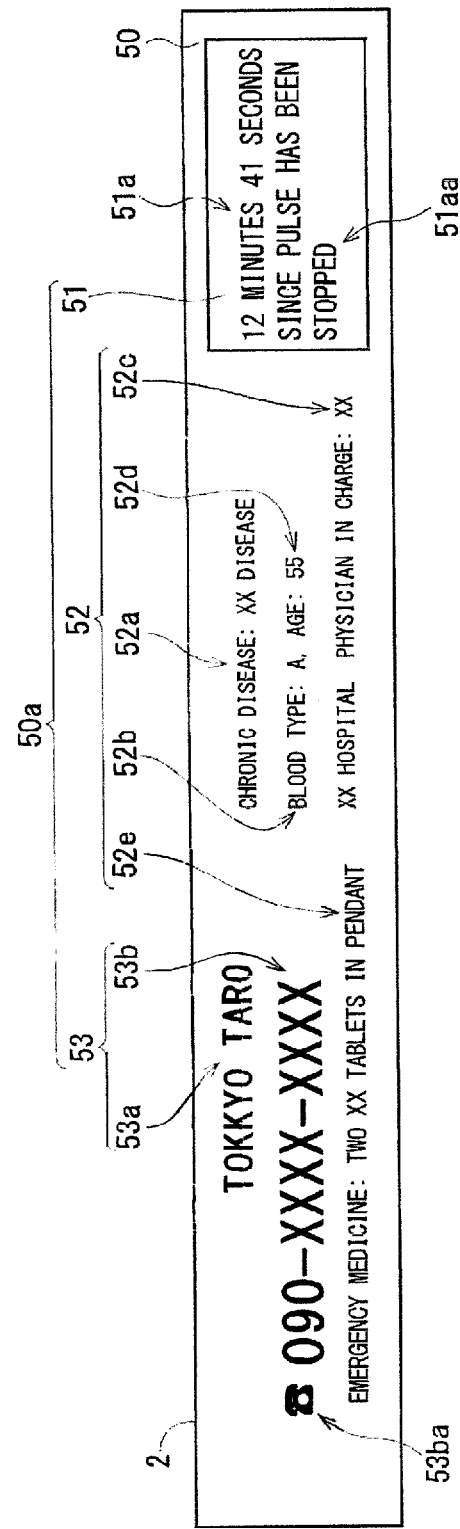
FIG. 13 schematically illustrates an example abnormality notification screen.

In the exemplification of FIG. 10, although the second information 52 includes the chronic disease name 52a, the blood type 52b, and the attending physician information 52c of the user, it may include at least one of these. Furthermore, the second information 52 may include information other than the chronic disease name 52a, the blood type 52b, and the attending physician information 52c of the user. FIG. 13 schematically illustrates an example of the abnormality notification screen 50. In the abnormality notification screen 50 illustrated in FIG. 13, the second information 52 further includes an age 52d and medicine information 52e of the user. The medicine information 52e is, for example, information on the medicine for the chronic disease of the user, and contains information such as a name and a possessing location of the medicine. Accordingly, the person who takes an action for the user can take a more appropriate action for the user, for example, making the user take some medicine based on the medicine information 52e.

Although the abnormality determining unit 104 determines that the biological information of the user contains an abnormality when the value of the biological information of the user becomes zero in the examples above, it may determine whether the biological information of the user contains an abnormality in the other methods. The abnormality determining unit 104 may determine that the biological information is abnormal, for example, when the value of the biological information input from the biological information obtaining unit 8 is out of a predetermined range. In other words, the abnormality determining unit 104 may determine that the biological information is abnormal when the value of the biological information of the user is smaller than a lower limit and when the value is larger than an upper limit.

Figure 14:
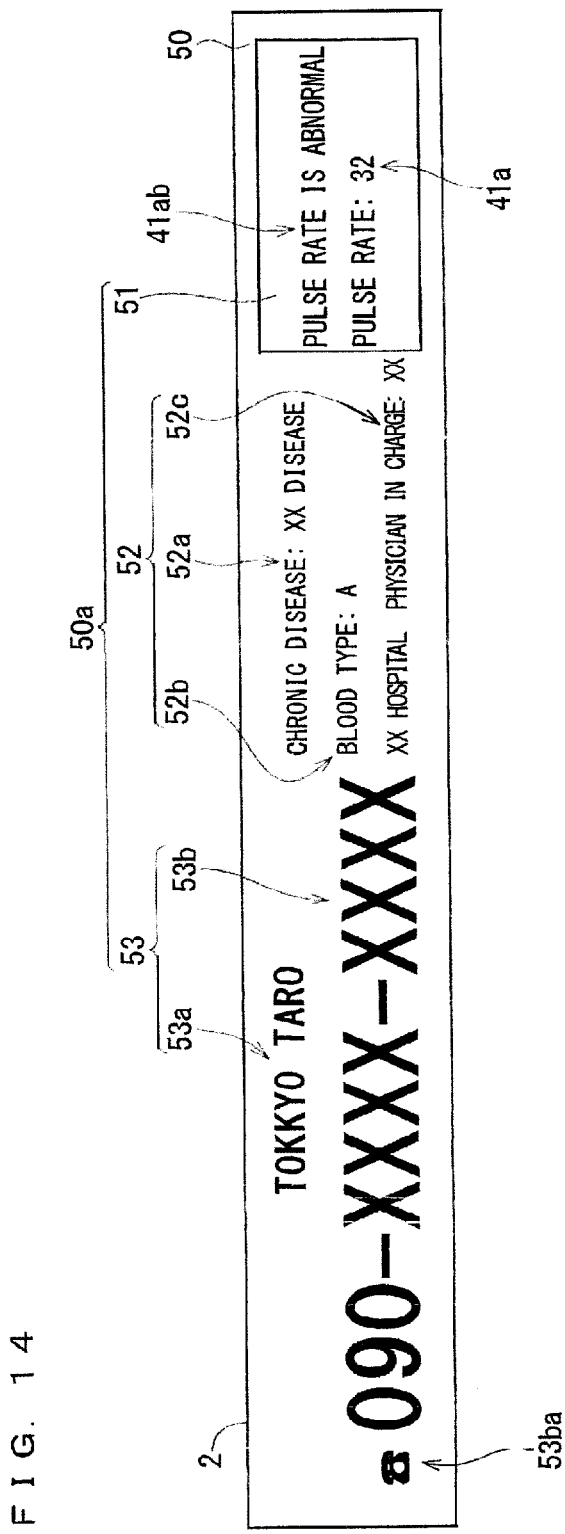
FIG. 14 schematically illustrates an example abnormality notification screen.

FIG. 14 schematically illustrates an example of the abnormality notification screen 50 to be displayed when the value of the biological information of the user is out of the predetermined range. As illustrated in FIG. 14, the first information 51 includes a number 41a indicating a pulse rate, and a character string 41ab indicating that the number 41a is abnormal.

The predetermined range with which the abnormality determining unit 104 determines whether the biological information of the user contains an abnormality is set according to, for example, a health condition of the user, and is stored in the storage 102.

Furthermore, although the electronic apparatus 1 obtains one kind of biological information in the examples above, the electronic apparatus 1 may obtain plural kinds of biological information. The biological information obtaining unit 8 may obtain, for example, a body temperature of the user besides a pulse rate. Here, the biological information obtaining unit 8 includes a temperature sensor that senses a body temperature of the user.

FIG. 15 schematically illustrates an example of the normal screen 40 including a pulse rate and a body temperature of the user. As illustrated in FIG. 15, the information 41 including the biological information of the user includes the number 41a indicating the pulse rate obtained by the biological information obtaining unit 8 and a number 41b indicating a body temperature.

Figure 16:
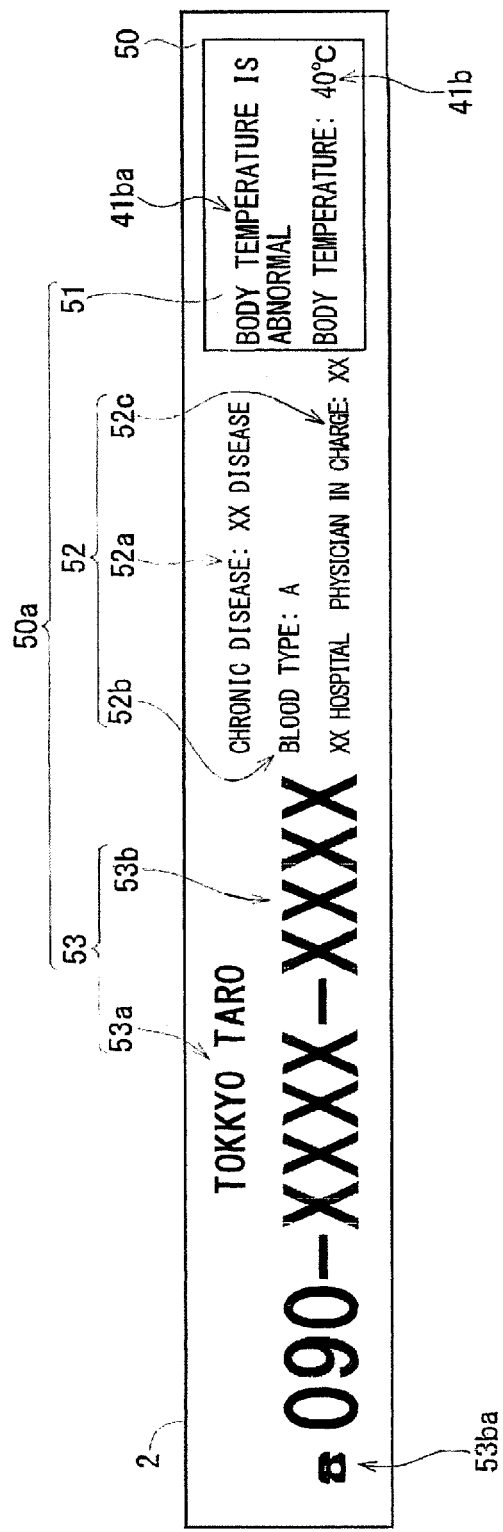
FIG. 16 schematically illustrates an example abnormality notification screen.

In the case where the biological information obtaining unit 8 obtains a body temperature, the abnormality determining unit 104 may determine that the body temperature is abnormal when the body temperature obtained by the biological information obtaining unit 8 is out of a predetermined range. FIG. 16 schematically illustrates an example of the abnormality notification screen 50 for notifying that the body temperature is abnormal. As illustrated in FIG. 16, the first information 51 includes the number 41b indicating a body temperature, and a character string 41ba indicating that the number 41b is abnormal.

Although the non-wearing time screen 30 in FIG. 8 and the normal screen 40 in FIG. 9 include some information, they may have no information, that is, no information may be displayed on the display 2 when the electronic apparatus 1 is not worn by the user and is in a normal time (when the electronic apparatus 1 is worn by the user and no abnormality occurs in the user). Here, only when it is determined that the biological information of the user contains an abnormality, information is displayed on the display 2. Thus, since information such as the time information 32 does not have to be displayed when the electronic apparatus 1 is not worn and is in the normal time, the power consumption of the electronic apparatus 1 can be reduced. Furthermore, one of the non-wearing time screen 30 and the normal screen 40 may include no information.

Furthermore, when no information is displayed on the display 2, for example, information such as the information 41 including the time information 32 or biological information may be displayed on the display 2 upon the operation button 4 being pressed once, whereas the abnormality notification screen 50 may be displayed on the display 2 upon the operation button 4 being pressed twice. Here, the information displayed on the display 2 upon the operation button 4 being pressed once may be deleted after a lapse of a predetermined period (for example, several hours). The operations on the operation button 4 are not limited to the ones described above. For example, information such as the information 41 including the time information 32 or biological information may be displayed on the display 2 when a period during which the operation button 4 is pressed is shorter than a predetermined period (pressed short), whereas the abnormality notification screen 50 may be displayed on the display 2 when a period during which the operation button 4 is pressed is longer than a predetermined period (pressed long).

While the electronic apparatus 1 is described in detail above, the foregoing description is in all aspects illustrative and not restrictive. The various modifications described above may be combined with one another and are applicable unless any contradiction occurs. It is understood that numerous modifications that have not yet been described can be devised without departing from the scope of the present disclosure.

The invention claimed is:

1. An electronic apparatus worn on a body of a user, the electronic apparatus comprising:
    a biological information obtaining unit to obtain biological information indicating a health condition of the user;
    at least one processor configured to determine whether the biological information of the user contains an abnormality; and
    a display on which an abnormality notification screen is displayed when the at least one processor determines that the biological information contains the abnormality, the abnormality notification screen providing a notification of the abnormality in the user,
    wherein the at least one processor determines an occurrence time at which the abnormality has occurred in the user and measures an elapsed time since the occurrence time of the abnormality in the user,
    the electronic apparatus is driven by a battery, when a voltage of the battery, detected by a battery voltage detector of the electronic apparatus, becomes smaller than a threshold, the abnormality notification screen displays the occurrence time at which the abnormality has occurred in the user on the display, and when the voltage of the battery is not smaller than the threshold, the abnormality notification screen displays the elapsed time since the occurrence time of the abnormality in the user on the display.

2. The electronic apparatus according to claim 1, wherein the abnormality notification screen comprises useful information that is useful in taking an appropriate action for the user in response to the abnormality.

3. The electronic apparatus according to claim 2, wherein the useful information comprises at least one of a chronic disease name, a blood type, and attending physician information relevant to an attending physician of the user.

4. The electronic apparatus according to claim 2, wherein the useful information comprises a name and a contact of the user.

5. The electronic apparatus according to claim 1, further comprising a transmitting unit to wirelessly transmit a notification signal notifying the abnormality in the user when the at least one processor determines that the biological information contains the abnormality.

6. The electronic apparatus according to claim 5, wherein the notification signal comprises position information indicating a position of the electronic apparatus.

7. The electronic apparatus according to claim 1, wherein the display is an electronic paper.

8. The electronic apparatus according to claim 1, wherein the abnormality notification screen is displayed on the display when the user performs a predetermined operation to the electronic apparatus, irrespective of a result of the determination whether the biological information of the user contains the abnormality.

9. The electronic apparatus according to claim 1, wherein the electronic apparatus outputs at least one of light and sound when the at least one processor determines that the biological information contains the abnormality.

10. The electronic apparatus according to claim 1, wherein a normal screen does not include user information relevant to the user except for the biological information, the normal screen being displayed on the display when the at least one processor determines that the biological information does not contain the abnormality.

* * * * *